US006325989B1

(12) United States Patent
Duke-Cohan et al.

(10) Patent No.: US 6,325,989 B1
(45) Date of Patent: *Dec. 4, 2001

(54) FORM OF DIPEPTIDYLPEPTIDASE IV (CD26) FOUND IN HUMAN SERUM

(75) Inventors: Jonathan S. Duke-Cohan, Cambridge; Chikao Morimoto, Needham; Stuart F. Schlossman, Fox Place, all of MA (US)

(73) Assignee: Dana-Farber Cancer Institute, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/457,694

(22) Filed: Jun. 1, 1995

(51) Int. Cl.[7] .............................. A61B 5/055; C12N 9/00; C12N 9/48
(52) U.S. Cl. ...................... 424/9.34; 435/183; 435/212
(58) Field of Search ................................. 424/85.1, 184.1; 514/8; 530/395; 435/183, 212

(56) References Cited

PUBLICATIONS

Fahey et al., Clin. & Exp. Immunol., vol. 88: 1–5, Jan. 1992.*
Hirsch et al., New England Journal of Medicine, vol. 328: 1686–1695, Jun. 1993.*
Callebaut et al., Science, vol. 262: 2045–2050, Dec. 1993.*
Scott et al., Leukemia Research, vol. 12: 129–134, Feb. 1988.*
Duke–Cohan et al., J. of Immunology, vol. 156: 1714–1721, Aug. 1996.*
Lerner, Nature, vol. 299: 592–596, Oct. 1982.*
Fox et al., "Ta[1], A Novel 105 KD Human T Cell Activation Antigen Defined By A Monoclonal Antibody," *J. Immunol.* 133:1250–1256 (1984).
Morimoto et al., 1F7, A Novel Cell Surface Molecule, Involved In Helper Function Of CD4 Cells, *J. Immunol.* 143:3430–3439 (1989).
Hafler et al., "Antigen Reactive Memory T Cells Are Defined By Ta[1][1] ," *J. Immunol.* 137:414–418 (1986).
Stein et al., "Leukocyte Typing IV" (Knapp, W., Oxford University Press, Oxford, Great Britian pp. 412–415 (1989).
Hegen et al., "The T Cell Triggering Molecule Tp103 Is Associated With Dipeptidyl Aminopeptidase IV Activity[1]," *J. Immunol.* 144:2908–2914 (1990).
Ulmer et al., "CD26 Antigen is a Surface Dipeptidyl Peptidase IV (DPPIV) as Characterized by Monoclonal Antibodies Clone TII–19–4–7 and 4EL1C7," *Scand. J. Immunol.* 31:429–435 (1990).
Tanaka et al., "The costimulatory activity of the CD26 antigen requires dipeptidyl peptidase IV enzymatic activity," *Proc. Natl. Acad. Sci. USA* 90:4586–4590 (1993).

Yaron et al., "Proline–Dependent Structural and Biological Properties of Peptides and Proteins," *Crit. Rev. Biochem. Mol. Biol.* 28:31–81 (1993).
Heymann et al., "Liver Dipeptidyl Aminopeptidase IV Hydrolyzes Substance P," *FEBS Lett.* 91:360–364 (1978).
Dang et al., "Comitogenic Effect of Solid–Phase Immobilized Anti–1F7 On Human CD4 T Cell Activation Via CD3 And CD2 Pathways[1] ," *J. Immunol.* 144:4092–4100 (1990).
Tanaka et al., "Cloning and Functional Expression of the T Cell Activation Antigen CD26[1]," *J. Immunol.* 149:481–486 (1992).
Torimoto e tal., Coassociation of CD26 (Dipeptidyl Peptidase IV) With CD45 On The Surface Of Human T Lymphocytes[1], *J. Immunol.* 147:2514–2517 (1991).
Kameoka et al., "Direct Association of Adenosine Deaminase with a T Cell Activation Antigen, CD26," *Science* 261:466–469 (1993).
Buc et al., "Influence of adenosine deaminase inhibition on the phosphoinositide turnover in the initial stages of human T cell activation*," *Eur. J. Immunol.* 20:611–615 (1990).
Tanaka et al., "Enhancement of antigen–induced T–cell proliferation by soluble CD26/dipeptidyl peptidase IV," *Proc. Natl. Acad. Sci.* (*USA*) 91:3082–3086 (1994).
Torimoto et al., "Biochemical Characterization Of CD26 (Dipeptidyl Peptidase IV): Functional Comparison Of Distinct Epitopes Recognized By Various Anti–CD26 Monoclonal Antibodies," *Mol. Immunol.* 29:183–192 (1992).
Morrison et al., "A Marker for Neoplastic Progression of Human Melanocytes Is a Cell Surface Ectopeptidase," *J. Exp. Med.* 177:1135–1143 (1993).
Kyouden et al., "Purification and Characterization of Dipeptidyl Peptidase IV in Rat Liver Lysosomal Membranes[1]," *J. Biochem.* 111:770–777 (1992).
Hino et al., "X–Prolyl Dipeptidyl–Aminopeptidase Activity, with X–Proline p–Nitroanilides as Substrates, in Normal and Pathological Human Sera," *Clin. Chem.* 22:1256–1261 (1976).
Vanhoof et al., "Distribution of Proline–Specific Aminopeptidases in Human Tissues and Body Fluids," *Eur. J. Clin. Biochem.* 30:333–338 (1992).

(List continued on next page.)

Primary Examiner—Ponnathapu Achutamurthy
Assistant Examiner—Manjunath N. Rao
(74) Attorney, Agent, or Firm—Fish & Richardson P.C.

(57) ABSTRACT

A soluble form of CD26 isolated from human serum is disclosed. The serum form shares similar enzymatic and antigenic properties with the membrane form. However, in several biochemical aspects there are distinct differences. In particular, the soluble serum form has a molecular weight of 175 kDa (in contrast to the 105 kDa molecular weight of the membrane form), and it does not bind Adenosine Deaminase Type-1. Nevertheless, the soluble form expresses functional dipeptidylpeptidase IV activity and retains the ability to costimulate the T lymphocyte response to recall antigen. Although 105 kDa membrane type CD26 may be found in the serum in small amounts, the majority of serum DPPIV activity is provided by a novel peptidase structurally distinct from membrane C26/DPPIV.

13 Claims, 8 Drawing Sheets

OTHER PUBLICATIONS

Stancikova et al., "Dipeptidyl peptidase IV in patients with systemic lupus erythematosus," *Clin. Exp. Rheumatol.* : 10:381–385 (1992).

Hama et al., "Changes in form of dipeptidyl–aminopeptidase IV in urine from patients with renal disease," *Clin. Chim. Acta.* 113:217–221 (1981).

Chikuma et al., "Purification and Properties of Dipeptidyl Peptidase IV from Human Urine," *Biol. Chem. Hoppe–Seyler* 371:325–330 (1990).

Fleischer et al., "CD26: a surface protease involved in T–cell activation," *Immunology Today* 15:180–184 (1994).

Schrader et al., "Purification of an Adenosine Deaminase Complexing Protein from Human Plasma," *J. Biol. Chem.* 254:11964–11968 (1979).

Darmoul et al., "Isolation of a cDNA probe for the human intestinal depeptidylpeptidase IV and assignment of the gene locus DPP4 to chromosome 2," *Ann. Hum. Genet.* 54:191–197 (1990).

Chobert et al., "Tissue–specific Expression of Two γ–Glutamyl Transpeptidase mRNAs with Alternative 5' Ends Encoded by a Single Copy Gene in the Rat*," *J. Biol. Chem.* 265:2352–2357 (1990).

Wada et al., Differential expression of two distinct forms of mRNA encoding members of a dipeptidyl aminopeptidase family, *Proc. Natl. Acad. Sci. (USA)* 89:197–201 (1992).

Scanlan et al., "Molecular cloning of fibroblast activation protein α, a member of the serine protease family selectively expressed in stromal fibroblasts of epithelial cancers," *Proc. Natl. Acad. Sci. (USA)* 91:5657–5661 (1994).

Bernard et al., "Structure of the Mouse Dipeptidyl Peptidase IV (CD26) Gene," *Biochemistry* 33:15204–15214 (1994).

Ollis et al., "The α/β hydrolase fold," *Protein Engineering* 5:197–211 (1992).

Hirschhorn et al., "Isozymes: Current Topics in Biological and Medical Research," 4:131–157 (1980).

Niedzwicki et al., "Plasma Adenosine Deaminase$_2$ Is a Marker for Human Immunodeficiency Virus–1 Seroconversion," *Am. J. Hematol.* 37:152–155 (1991).

Ungerer et al., "Serum Adenosine Deaminase: Isoenzymes and Diagnostic Application," *Clin. Chem.* 38:1322–1326 (1992).

Matsuda et al., "Serum Adenosine Deaminase 2 and Neopterin Levels Are Increased in a Majority of Hemophiliacs of Infection with Human Immunodeficiency Virus Type I," *Clin. Infec. Dis.* 16:260–264 (1993).

* cited by examiner

SEQUENCE LISTING

<160> NUMBER OF SEQ ID NOS: 12

<210> SEQ ID NO 1
<211> LENGTH: 15
<212> TYPE: PRT
<213> ORGANISM: Homo sapiens

<400> SEQUENCE: 1

Leu Thr Gly Ser Ser Gly Phe Thr Asp Gly Pro Gly Asn Tyr Lys
1               5                   10                  15

<210> SEQ ID NO 2
<211> LENGTH: 12
<212> TYPE: PRT
<213> ORGANISM: Homo sapiens
<220> FEATURE:
<221> NAME/KEY: VARIANT
<222> LOCATION: (1)...(12)
<223> OTHER INFORMATION: Xaa = Any Amino Acid

<400> SEQUENCE: 2

Tyr Asp Val Asp Thr Gln Met Xaa Thr Ile Leu Lys
1               5                   10

```
<210> SEQ ID NO 3
<211> LENGTH: 7
<212> TYPE: PRT
<213> ORGANISM: Homo sapiens

<400> SEQUENCE: 3

Gly Phe Asn Leu Ile Ile Thr
 1               5

<210> SEQ ID NO 4
<211> LENGTH: 9
<212> TYPE: PRT
<213> ORGANISM: Homo sapiens

<400> SEQUENCE: 4

Gln Asn Ala Leu Leu Ala Arg Leu Thr
 1               5

<210> SEQ ID NO 5
<211> LENGTH: 20
<212> TYPE: PRT
<213> ORGANISM: Homo sapiens

<400> SEQUENCE: 5

Gly Asp Gln His Thr Asp Cys Tyr Ser Cys Thr Ala Asn Thr Asn Asp
 1               5                  10                  15

Cys His Trp Cys
            20

<210> SEQ ID NO 6
<211> LENGTH: 8
<212> TYPE: PRT
<213> ORGANISM: Homo sapiens

<400> SEQUENCE: 6

Ser Gly Gln Ile Ser Ile Phe Gly
 1               5

<210> SEQ ID NO 7
<211> LENGTH: 16
<212> TYPE: PRT
<213> ORGANISM: Leishmania

<400> SEQUENCE: 7

Val Arg Gly Ser Ser Gly Tyr Val Ala Cys Thr Pro Gly Gln Arg Val
 1               5                  10                  15

<210> SEQ ID NO 8
<211> LENGTH: 12
<212> TYPE: PRT
<213> ORGANISM: Homo sapiens

<400> SEQUENCE: 8

Tyr Asp Ala Glu Asn Lys Leu Asn Asp Ile Leu Leu
 1               5                  10

<210> SEQ ID NO 9
<211> LENGTH: 7
<212> TYPE: PRT
<213> ORGANISM: Bacillus brevis

<400> SEQUENCE: 9

Gly Phe Asn Leu Ile Thr Lys
 1               5
```

```
<210> SEQ ID NO 10
<211> LENGTH: 9
<212> TYPE: PRT
<213> ORGANISM: Homo sapiens

<400> SEQUENCE: 10

Met Arg Ala Leu Leu Ala Arg Leu Leu
 1               5

<210> SEQ ID NO 11
<211> LENGTH: 21
<212> TYPE: PRT
<213> ORGANISM: Homo sapiens

<400> SEQUENCE: 11

Pro Gln Asn Glu Arg Gln Cys Tyr Ser Cys Lys Gly Asn Ser Thr His
 1               5                  10                  15

Gly Cys Ser Ser Glu
            20

<210> SEQ ID NO 12
<211> LENGTH: 8
<212> TYPE: PRT
<213> ORGANISM: Homo sapiens

<400> SEQUENCE: 12

Ser Gly His Ile Cys Ile Phe Glu
 1               5
```

FORM OF DIPEPTIDYLPEPTIDASE IV (CD26) FOUND IN HUMAN SERUM

GOVERNMENT RIGHTS

This invention was made at least in part with funds provided under grants from the United States Government (National Institutes of Health Grants AI23360-08, AI12069, CA55601 and CA34183). Therefore, the U.S. Government has certain rights in this invention.

FIELD OF THE INVENTION

This invention relates to human T cell activation antigens.

BACKGROUND OF THE INVENTION

Human CD26, a Type II membrane glycoprotein with intrinsic dipeptidylpeptidase IV (DPPIV) activity and ability to bind Adenosine Deaminase Type I (ADA-1), is expressed on epithelial cells constitutively, but on T lymphocytes its expression is regulated.

Initially identified as a 105 kDa T cell activation antigen defined by the monoclonal antibody Ta1 (1), the CD26 antigen was subsequently shown to delineate the T cell subset responding to recall antigens (2, 3). Although the antigen is expressed in the liver, kidney and intestine (4), only in the T cell are the levels of membrane CD26 under tight cellular regulation with expression upregulated upon cell activation. CD26 has been shown to have dipeptidylpeptidase IV activity (DPPIV, EC 3.4.14.5) in its extracellular domain (5, 6) and the costimulatory potential appears to be partially dependent upon this enzyme activity (7) which can cleave amino terminal dipeptides with proline, and less effectively, alanine in the penultimate position (8). Although a substrate of relevance to T cell activation has not yet been identified, other substrates, including the neuropeptide substance P, may be processed in vivo by DPPIV/CD26 (9).

CD26 not only marks the activated state but is itself involved in the signal transducing process: crosslinking of CD3 and CD26 results in enhanced T cell activation in the absence of antigen-presenting cells (10). It is unlikely that CD26 is directly involved in transducing the activation signal across the T cell membrane since it has only a very short cytoplasmic region of 6 amino acids (11). The protein tyrosine phosphatase, CD45RO, has been shown to associate with CD26 and may provide a putative mechanism for the costimulation (12). Other associations include the strong binding of Adenosine Deaminase Type I (ADA-1) to CD26 (13). This may be of particular importance since ADA activity helps regulate the early stages of signal transduction in T lymphocytes (14). That the costimulatory potential of CD26 occurs extracellularly has been confirmed by showing that a soluble recombinant CD26 (rsCD26) representing the extracellular domain can enhance the T cell-mediated reaction to recall antigens (15). Reinforcing the proposal that soluble CD26 is costimulating, it has been found that in the absence of recall antigen, the rsCD26 has no effect upon the proliferative response. A natural form of soluble DPPIV/CD26 can be identified in normal human serum. The levels of this naturally-occurring soluble DPPIV influenced the level of reactivity of T cells to recall antigens (15).

SUMMARY OF THE INVENTION

We have now isolated soluble DPPIV/CD26 from human serum and have unexpectedly determined that while the serum form shares similar enzymatic and antigenic properties with the membrane form, in several biochemical aspects there are distinct differences. In particular, the soluble form has a molecular weight of 175 kDa, and it does not bind ADA-1. Nevertheless, it retains the ability to costimulate the T lymphocyte response to the recall antigen, tetanus toxoid. Furthermore, N-terminal sequencing of the resulting peptides after tryptic digestion suggested structural disparity between membrane CD26 and soluble serum DPPIV. Accordingly, we suggest that although 105 kDa membrane type CD26 may be found in the serum in small amounts, the majority of serum DPPIV activity is provided by a novel peptidase structurally distinct from DPPIV/CD26.

Thus, in one aspect the invention features a substantially purified glycoprotein, a monomer of the glycoprotein having a molecular weight of approximately 175 kDa, of which approximately 130 kDa is the unglycosylated moiety. The glycoprotein of the invention has an antigenic determinant or determinants immunologically cross-reactive with determinants of CD26, is capable of expressing functional dipeptidylpeptidase IV (DPPIV) activity, but is not capable of binding Adenosine Deaminase Type-1 (ADA-1). Preferably, the glycoprotein of the invention exists in the form of a trimer and contains N-linked glycosylation but not O-linked glycosylation.

By "substantially pure" is meant a polypeptide or protein which has been separated from biological macromolecules (e.g., other proteins, carbohydrates, etc.) with which it naturally occurs. Typically, a protein or polypeptide of interest is substantially pure when less than 25% (preferably less than 15%) of the dry weight of the sample consists of such other molecules.

The invention furthermore features the unglycosylated moiety of the above glycoprotein as a substantially purified protein having a molecular weight of approximately 130 kDa.

Also featured is a therapeutic composition containing the DPPIV/CD26 glycoprotein of the invention in a pharmaceutically acceptable carrier (e.g., saline or any aqueous or nonaqueous substance which is suitable for injection). Such a therapeutic composition can be used in a method for modulating the immune response of a patient (e.g., enhancing the immune response of an immunosuppressed patient) by administering the composition to the patient by an appropriate means. It is expected to be particularly useful for the treatment of immunosuppression in a patient infected with human immunodeficiency virus (HIV) and having the acquired immune deficiency syndrome (AIDS) or AIDS-related complex, but may also be used where the patient's immune system is depressed as a result of treatment with an immunosuppressive compound, or acquired immunodeficiency of undetermined etiology, or congenital immunodeficiency. The soluble, naturally occuring high molecular weight form of DPPIV/CD26 disclosed herein will be particularly useful because the type and extent of glycosylation is the naturally occuring pattern. Therefore, the high molecular weight form should have a longer half life than any soluble recombinant form of CD26.

The compounds of the invention, when combined with a pharmaceutically acceptable carrier, are also useful as vaccine adjuvants, to be administered to an individual vaccinee in conjunction with (i.e., immediately before, after, or along with) a vaccine antigen in order to enhance the immune response produced by such antigen. Examples of vaccine antigens which may be used with the adjuvant of the invention include those containing chemically inactivated or genetically engineered viral or bacterial products, such as diptheria or pertussin toxoid or recombinant viral proteins, and those containing live but attenuated virus or bacteria.

Fragments of serum soluble DPPIV/CD26 can be assayed for costimulatory activity. One such assay would include the following steps: (a) contacting a lymphocyte with a candidate fragment of serum soluble DPPIV/CD26, and (b) determining whether the fragment increases the rate of proliferation of the lymphocyte in response to antigenic stimuli, such increase being an indication of costimulatory activity.

In another aspect the invention features an antibody, whether polyclonal or monoclonal, that binds to the 175 kDa form but not the 105 kDa form of DPPIV/CD26. Such an antibody is useful in differentiating these two forms of DPPIV/CD26 and can serve as a diagnostic agent in a method for detecting the presence of the 175 kDa form as a diagnostic marker of T cell activation. Quantitative determination of the presence of the 175 kDa form of DPPIV/CD26 can serve as a precise measure of disease activity in disorders of the immune system.

The invention also features nucleic acid encoding 175 kDa DPPIV/CD26, which is useful for transferring expression of the 175 kDa form, either in vivo or in vitro, to cells lacking such capability.

Other features and advantages of the invention will be apparent from the following detailed description, and from the claims.

DETAILED DESCRIPTION OF THE INVENTION

Figures 1A, 1B, 1C:
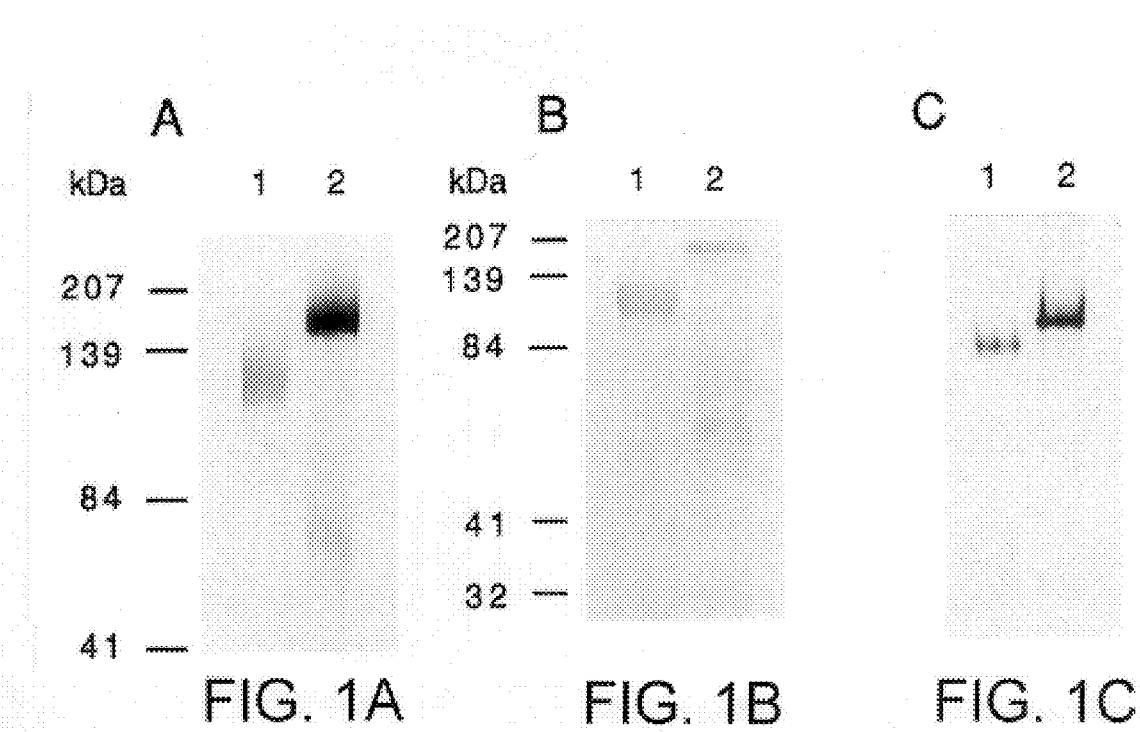
FIG. 1 shows the results of comparative electrophoretic analyses of rsCD26 and serum DPPIV/CD26 under various sets of conditions. Panel A: Analysis by SDS-PAGE (6%) under non-reducing conditions of rsCD26 (lane 1), and soluble serum DPPIV (lane 2). Panel B: Analysis by sodium dodecyl sulfate polyacrylamide gel electrophoresis SDS-PAGE (10%) under reducing conditions of rsCD26 (lane 1), and soluble serum DPPIV (lane 2). Panel C: Analysis by Tris-Glycine Native-PAGE (7.5%) of rsCD26 (lane 1), and soluble serum DPPIV (lane 2)

We identify and describe here the properties of a novel form of DPPIV/CD26 which is soluble in serum and distinct from the membrane form. We show that serum DPPIV exists naturally as trimer with a monomeric molecular weight of 175 kDa, in contrast to rsCD26, which has a monomeric molecular weight of 105–110 kDa. Serum DPPIV is probably a serine proteinase. Deglycosylation removed N-linked sugar from both serum DPPIV and rsCD26 and no O-linked glycosylation was observed, revealing a protein core of 130 kDa for serum DPPIV. The large serum form expresses functional DPPIV activity with similar substrate and inhibitor specificities and pH activity profile as rsCD26. Epitope analysis showed that monoclonal antibodies against five epitopes expressed by rsCD26 also bound, but more weakly, with serum DPPIV. Analysis of peptides after limited proteolysis and N-terminal sequencing revealed no homology with rsCD26 but some identity with other peptidases. Unlike rsCD26, the serum form does not bind ADA-1 and has no ADA-1 already associated with it. Similarly to rsCD26, serum DPPIV is a potent T cell costimulator. We conclude that the serum form of DPPIV is unique and is not a breakdown product of membrane CD26. The conservation of DPPIV activity and five epitopes specific to rsCD26 suggest, however, a significant structural similarity.

Purification of Serum Soluble DPPIV/CD26

The presence of soluble CD26 has been described previously in detergent-free cell extracts (23), and its presence has been inferred in serum from the identification of significant circulating DPPIV activity or by reactivity with defined anti-CD26 antibodies (15, 24–26). We have previously shown that serum soluble CD26/DPPIV may play an important role in regulating the immune response to recall antigens in vivo (15) and wished to confirm the identity of the serum form with the membrane form. Nevertheless, to clear serum of DPPIV activity using the high affinity anti-CD26 antibody 1F7 required large amounts of antibody, suggesting that there were structural differences between the membrane and soluble forms.

We thus set about purifying the DPPIV activity from human serum. Using both commercially available frozen serum as well as freshly isolated plasma, we developed a non-denaturing procedure for purifying the soluble DPPIV activity using techniques which were designed to maintain functional integrity. Although we had a large panel of antibodies available, we did not use these for affinity purification since we found that in every case the harsh elution conditions required (glycine-HCl, pH1–pH2, or 3M KSCN) resulted in a reduction in the DPPIV specific activity of at least one order of magnitude. In every purification, the DPPIV activity and anti-CD26 reactivity was associated with a homogenous band of 175 kDa obtained by preparative native gel electrophoresis. In two preparations (out of 7 total), we were also able to copurify some lower molecular weight DPPIV activity corresponding to the 105 kDa form of CD26, but quantitation by laser densitometry confirmed that this was always less than 6 % of the total preparation, and separated away at the preparative native electrophoresis stage.

Serum Soluble DPPIV/CD26 is Distinct from a Shed Form of 105 kDa Membrane CD26

Soluble DPPIV has been identified in pathological and normal human urine with a molecular weight of around 280 to 400 kDa determined by gel filtration (27, 28), although it is unlikely that the 400 kDa form represents a dimer of the serum form, since its size would not normally transfer by glomerular filtration. Kidney and epithelial-associated DPPIV/CD26 is a membrane dimer in the range 230–270 kDa (29) with reduced subunits of CD26 having a molecular weight of 105 kDa to 115 kDa, from which it is difficult to deduce any relationship with the serum form described here. One previous study purified an ADA-1 Complexing Protein (ADA-CP) of 105 kDa from human plasma (30), and their yield coincided with the small amounts of 105 kDa soluble CD26 we could isolate from some plasma samples (5–10 $\mu$g/100 ml serum). Nevertheless, their procedure utilized a polyclonal antibody developed against ADA-CP, and purification was monitored by ADA activity which would miss the larger non-ADA-binding form of DPPIV.

This raises the issue of the origin of large 175 kDa DPPIV in the serum. We have shown that the material in its reduced and deglycosylated form is larger than the membrane form. Therefore, it cannot result from shedding or proteolytic digestion of membrane CD26/DPPIV. Several mRNA species have been reported for human CD26 (11) although the evidence to date suggests that human DPPIV/CD26 is produced from a single location on chromosome 2 (31), perhaps allowing alternative splicing as a possible origin of serum CD26. One further possibility is that initiation occurs at two distinct promoter sites, as has already been shown for another membrane ectoenzyme, rat $\gamma$-glutamyl transpeptidase (32). There is also support for a distinct separate gene since DPP-X has been observed which shows great homology to DPPIV, but does not exhibit any dipeptidylpeptidase IV activity itself (33). Further evidence that there may be disparate genes coding for CD26-like molecules is provided by the recent report that Fibroblast Activation Protein-$\alpha$ (FAP-$\alpha$) is a Type II membrane glycoprotein with remarkably similar sequence and organizational structure to membrane CD26 and, in fact, can form a heterodimer with membrane CD26 (34).

We may safely exclude the possibility that the DPPIV activity is the result of contaminating 105 kDa soluble CD26 or other aminopeptidases which may release the substrate chromophore by sequential degradation. The levels of aminopeptidase P in serum are essentially zero (25), while aminopeptidase M (CD13) activity could not be detected (by hydrolysis of Leu-pNA). Furthermore, the substrate specificities, inhibitor kinetics, and pH optimum of serum DPPIV were very similar to those of rsCD26.

Antigenic Similarity Between Serum and Membrane Forms of CD26

Epitope analysis revealed that monoclonal antibodies against five epitopes expressed by rsCD26 also bound serum DPPIV. However, one of the differences between the serum and membrane forms was in the relative expression of epitopes detected by these monoclonal anti-CD26 antibodies. Although these epitopes were expressed by the large 175 kDa DPPIV, the antibodies bound more strongly to rsCD26. This made itself apparent particularly in a previous report by our group where very high concentrations of 1F7 antibody (40 $\mu$g/ml) were required to clear DPPIV activity and CD26 antigenic activity from the serum (15). Nevertheless, the eventual complete clearance of DPPIV activity by this antibody, albeit at high concentrations, also implies that all the DPPIV activity in serum could be attributed to 1F7-reactive antigen and implies structural similarities between all functional DPPIV moieties in serum. In support, we have now produced a polyclonal rabbit antibody against purified serum DPPIV which binds strongly to Jurkat cells (CD26-negative) transfected with cDNA encoding the 105 kDa CD26/DPPIV (unpublished data). The N-terminal sequences of peptides released by protease treatment, however, suggest little sequence similarity between rsCD26 and serum DPPIV. Some caution must be exercised here since we may be comparing only those regions sensitive to proteolytic digestion; we have preliminary data that both proteins appear to have large protease-resistant regions. One recent report favors the notion that the DPPIV-related enzymes have arisen by divergent evolution from an $\alpha/\beta$-hydrolase ancestor, where distinct secondary and tertiary structures may be retained despite complete differences in sequence (35). In contrast, the disparity of sequence and conservation of structure between the eukaryotic serine proteases, cysteine proteases, subtilisins and the $\alpha/\beta$ hydrolase fold enzymes provides a strong argument for convergent evolution (36).

Affinity of Serum Soluble DPPIV/CD26 for ADA-1

A further difference between serum and recombinant CD26 concerns the inability of serum DPPIV to bind ADA-1. Human ADA exists as two forms, a low molecular weight (40 kDa) Type 1 form, and a high molecular weight (100 kDa) Type 2 form (37). ADA-1 accounts for almost all intracellular and membrane-associated ADA while ADA-2 is predominantly found circulating in the serum. Recent reports show that ADA-1 interacts strongly with the membrane form of CD26 (13, 22), and that CD26 is equivalent to what was previously reported as ADA-CP. ADA-2 is not well characterized, but its levels vary significantly with immune activity, particularly during opportunistic or systemic bacterial infections (38–40). There exists the possibility that serum DPPIV interacts with serum ADA-2 rather than with ADA-1, but this remains to be tested. Nevertheless, ADA-1 does not appear to play a role in the T cell costimulatory activity mediated by serum DPPIV since the non-ADA-1-binding serum DPPIV is a potent costimulator of recall-antigen driven T lymphocyte responses in vitro.

Cellular Origin of Serum Soluble DPPIV/CD26

Figure 7:
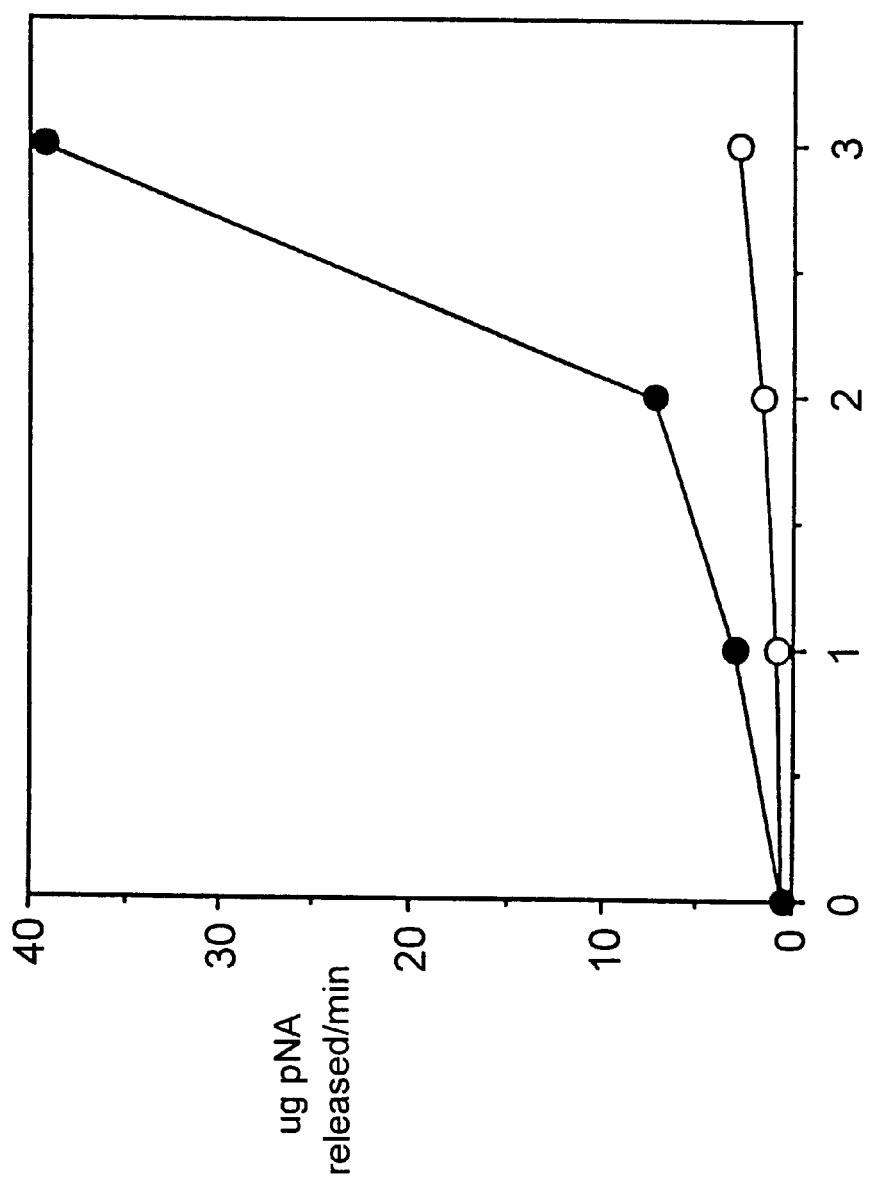
FIG. 7 is a graph showing the DPPIV activity of material released from activated T cells compared to resting T cells. Purified T cells were incubated for the indicated time with or without PHA, and the DPPIV activity released into serum-free medium was determined. All DPPIV activity is associated with a 175 kDa molecule.
Figure 8:
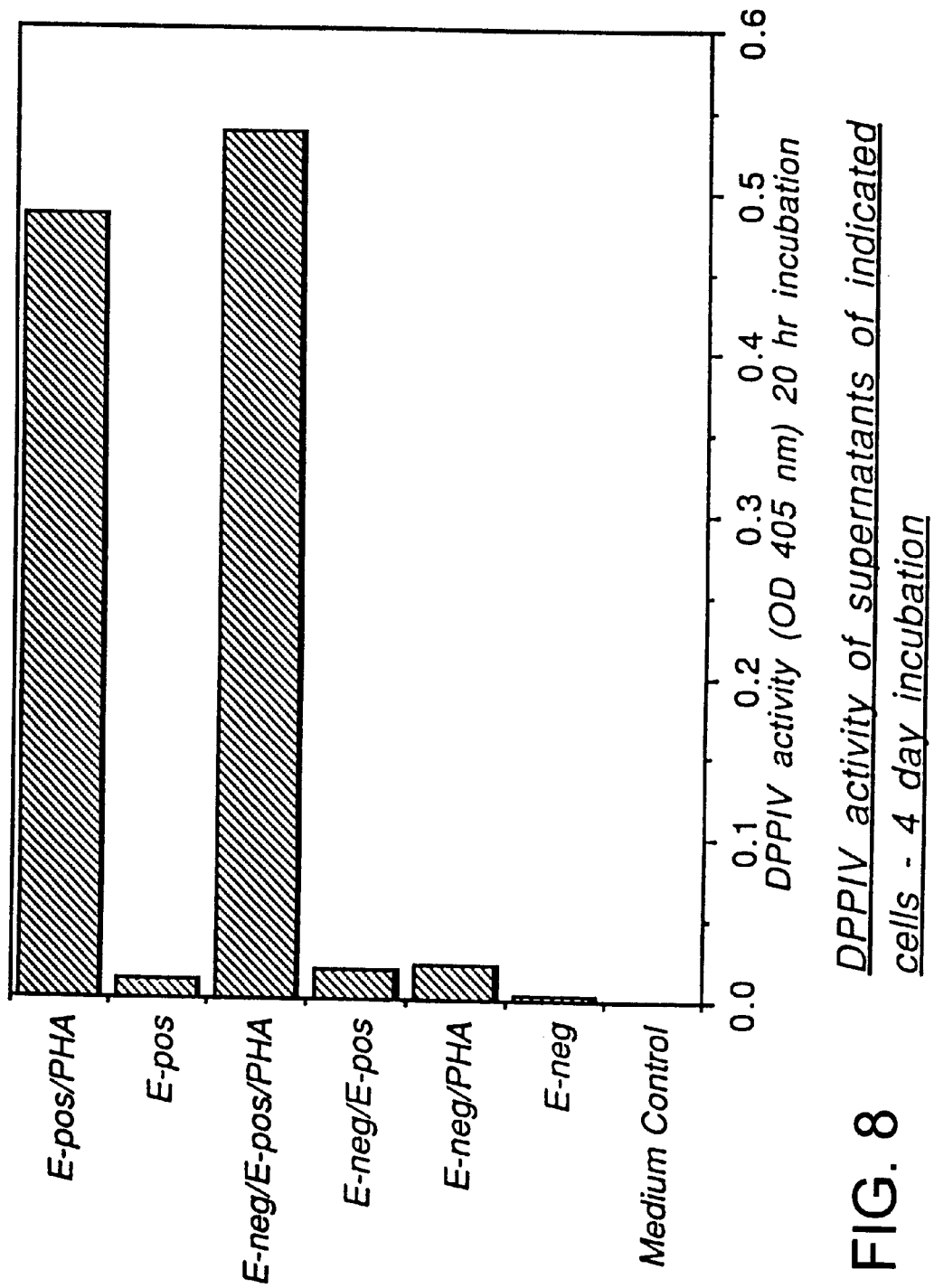
FIG. 8 shows the comparative ability of activated T cells, monocytes, macrophages and B cells to release DPPIV/CD26. T cells purified by sheep red blood cell resetting technique (E-pos) were mixed with or without monocytes and B cells (E-neg) with or without PHA for the indicated periods in serum-free medium and the released DPPIV activity was determined.

The intriguing similarities and differences between the serum form and the membrane form of DPPIV/CD26 suggest a common origin of these glycoproteins. The clear ability of both DPPIV/CD26 forms to enhance immune function supports the proposal that DPPIV/CD26 is an important regulator of the in vivo immune response, both as a membrane antigen and as a soluble serum protein. We next investigated whether both forms are present in the T lymphocyte and determined that PHA-activated T cells release a soluble protein showing DPPIV activity, whereas such a protein is not released from resting T cells (FIG. 7). The released material has a molecular weight of 175 kDa and appears to be identical in other respects with serum soluble DPPIV/CD26. Only activated T cells release a protein showing DPPIV activity. Referring to FIG. 8, we have shown that a soluble DPPIV/CD26 is not released by E-negative cells, specifically monocytes, macrophages and B cells, and the presence of such non-T immune cells does not enhance the release of 175 kDa DPPIV by T cells.

Figure 9:
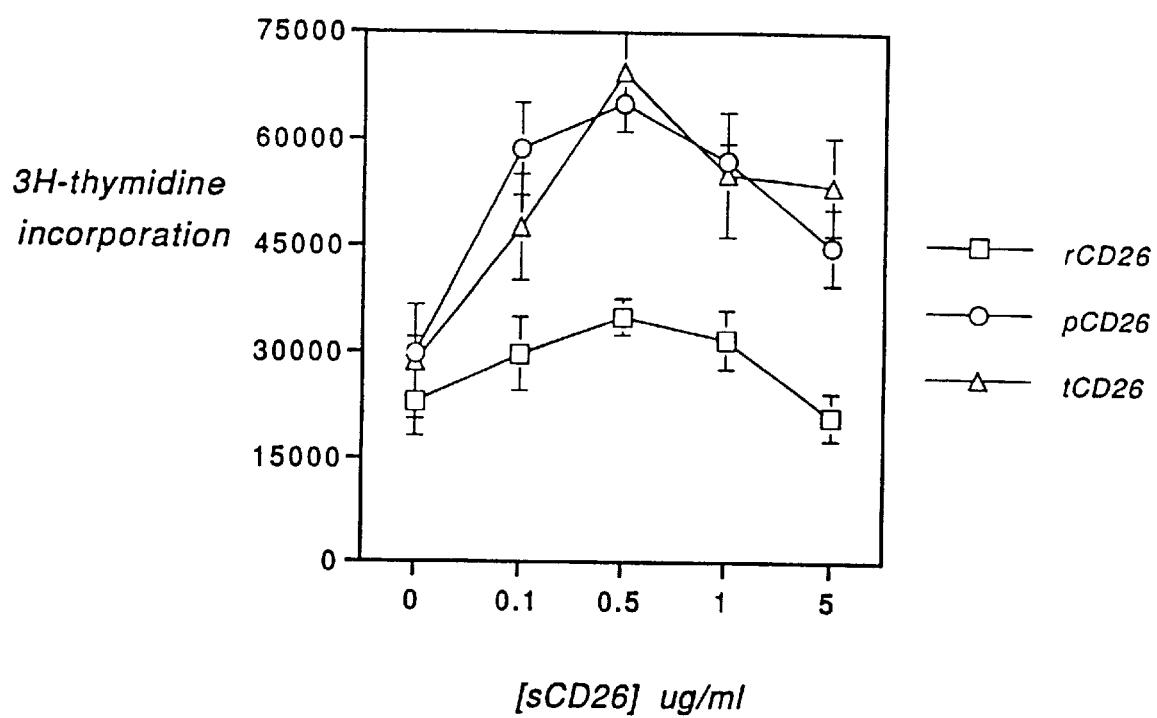
FIG. 9 shows the comparative ability of rsCD26, serum CD26/DPPIV and purified T cell-secreted DPPIV/CD26 to co-stimulate the response of normal T cells to recall antigen using similar conditions to those described in the legend to FIG. 6.

We then compared the activation potential of the various forms of DPPIV/CD26 we have prepared and determined that rsCD26, purified serum/plasma DPPIV/CD26 and purified T cell-secreted soluble DPPIV/CD26 all can costimulate the response of normal T cells to the recall antigen, tetanus toxoid (FIG. 9). Our results show that the serum/plasma form and the T cell-secreted form of DPPIV/CD26 are much more effective than the recombinant soluble form at enhancing the immune response in vitro, but nevertheless showed the identical kinetics of costimulation to those displayed by recombinant soluble CD26.

Isolation of Antibodies Capable of Distinguishing the 175 kDa Form of DPPIV/CD26 from the 105 kDa Form In order to distinguish the 175 kDa form of DPPIV/CD26 from the 105 kDa form, we have isolated an antibody that can bind specifically to 175 kDa DPPIV/CD26. This latter antibody is a polyclonal rabbit antibody against 175 kDa DPPIV/CD26 which was obtained after multiple immunisations of rabbits with the 175 kDa DPPIV/CD26. The rabbit serum was passed onto a Protein A-sepharose column to bind the immunoglobulin fraction, which was then eluted. The purified immunoglobulins contained antibody which could bind to cells expressing only the 105 kDa DPPIV/CD26 as well as to activated T cells expressing both the small and large forms of DPPIV/CD26. The purified immunoglobulin prepartion was then passed over a sepharose column to which had been immobilised recombinant solbule CD26. This procedure removes all the antibody directed against the 105 kDa DPPIV/CD26. The material passing through the column without binding was then tested again against a cell line expressing only the 105 kDa form, and no binding was observed. Nevertheless, the antibody could still bind to activated T cells expressing the large 175 kDa form, and this was confirmed by the ability of the antibody to immunoprecipitate the 175 kDa molecule with minimal immunoprecipitation of the soluble 105 kDa form.

These results show:

a) that the 175 kDa DPPIV/CD26 and 105 kDa DPPIV/CD26 share many common antigenic epitopes.

b) that the 175 kDa DPPIV/CD26 also expresses some unique epitopes not expressed on the 105 kDa DPPIV/CD26.

c) that, in using the rabbit antibody treated as described above (passage and elution from a Protein A-sepharose column followed by passage over a recombinant solbule CD26-sepharose column), we have an antibody which can specifically differentiate between the 105 kDa and 175 kDa forms of DPPIV/CD26, either as a marker on the surface of T cells, or for use in measuring plasma/serum concentrations utilizing a competitive radioimmunoassay or an equivalent technique. Quantitative detection of the 175 kDa form may serve as a precise measure of disease activity in disorders of the immune system.

Isolation of Nucleic Acid Encoding the 175 kDa Form of DPPIV/CD26

We will isolate a cDNA clone encoding 175 kDa DPPIV/CD26 by a simple and highly efficient cloning strategy based on transient expression in COS cells, a technique initially devised by Aruffo and Seed (Proc. Nat. Acad. Sci. USA 84:8573–7, 1987). Central to this strategy is the use of an efficient method to prepare large plasmid cDNA libraries. The libraries are introduced into COS cells, where transient expression of surface antigen allows the isolation of cDNAs by wasy of antibody binding. The transiently transfected cells grow as discrete colonies, each derived from a single transfected cell. Samples of the colonies are taken and probed for expression of 175kDa DPPIV/CD26. Positive colonies are isolated and the transfected DNA is recovered, and inserted into a suitable vector for amplification prior to sequencing.

The following examples are presented to illustrate the advantages of the present invention and to assist one of ordinary skill in making and using the same. These examples are not intended in any way otherwise to limit the scope of the disclosure.

EXAMPLE I

Purification of Serum DPPIV

DPPIV from serum was isolated by sequential purification using ion exchange chromatography (s-Sepharose), ConA affinity chromatography, and a second separation on s-Sepharose. Approximate levels of purification and yields are presented in Table 1. The chromatographic procedures yielded a preparation which displayed three protein bands by SDS/PAGE under reducing conditions. None of the bands co-migrated with the 105 kDa rsCD26. The preparation was further purified by eluting the three bands from a non-denaturing native preparative Tris-Glycine gel. All DPPIV enzyme activity was associated with a single high molecular weight band on the native gel which consisted predominantly of a 175–180 kDa moiety by non-reducing and reducing SDS-PAGE (FIGS. 1A, B). Under native conditions, the serum DPPIV activity migrated differently from rsCD26 (FIG. 1C). This preparation was further analyzed by matrix-assisted laser desorption mass spectrometry (21) which revealed a strong peak at approximately 175 kDa while rsCD26 produced a strong signal at 101–105 kDa. In addition, gel filtration chromatography on Superdex 200 revealed that in its native state, the serum DPPIV migrates between thyroglobulin (669 kDa) and apoferritin (443 kDa) as a large complex of 570 kDa. Since the material applied to the gel filtration column was not appreciably contaminated by any other protein, the serum DPPIV would appear to exist as a trimer. Due to availability, the DPPIV was purified from human serum rather than plasma. Nevertheless, purification of DPPIV from 50 ml plasma of 7 normal donors revealed an identical 175–180 kDa band. In two instances, the 105 kDa form copurified with the 175 kDa form, but was less than 6% of the total protein preparation by laser densitometry.

EXAMPLE II

Biochemical Characterization of Serum CD26/DPPIV

Figure 2:
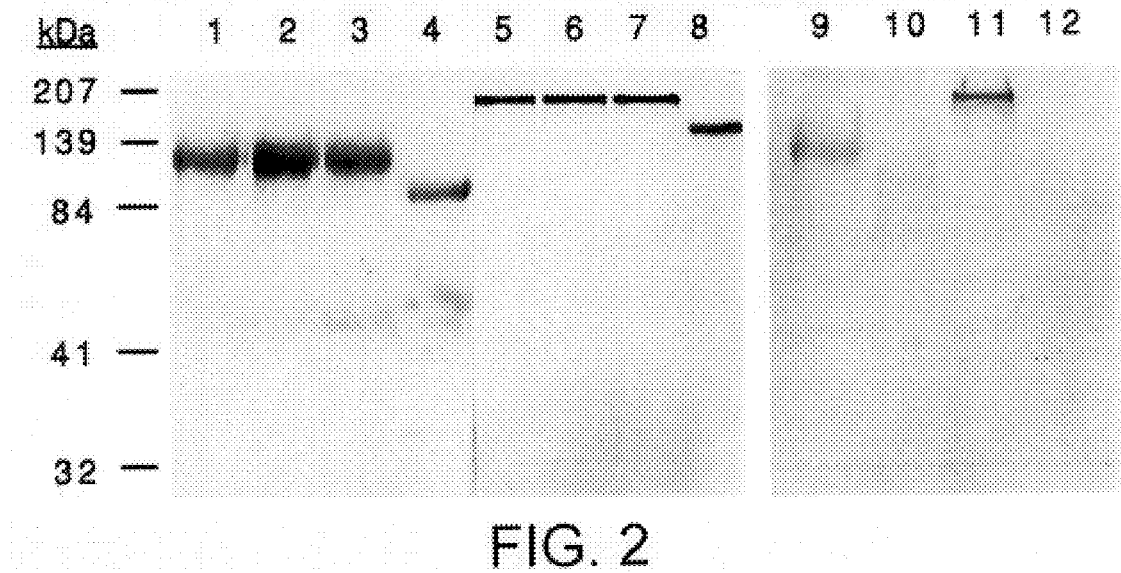
FIG. 2 shows the results of analysis of glycosylation of rsCD26 (Lanes 1–4) and soluble serum DPPIV (Lanes 5–8) by sequential enzymatic deglycosylation and separated on a 10% SDS-PAGE gel under reducing conditions followed by silver staining. Lanes 1 and 5: untreated sample. Lanes 2 and 6: removal of terminal NeuAc with NANase II. Lanes 3 and 7: NANase II and removal of O-linked sugars by O-Glycosidase. Lanes 4 and 8: NANase II, O-Glycosidase and removal of N-linked sugars by PNGase F. Lanes 9 and 10: Periodic acid-Schiff staining for glycoprotein of the same rsCD26 samples as in Lane 1 and lane 4, and lanes 11 and 12: glycoprotein staining of the same serum DPPIV samples as in lanes 5 and 8.

The membrane form of CD26 is heavily glycosylated (approximately 16% of the molecular weight (18) so we examined the pattern of glycosylation of the serum form to determine whether it resulted from hyper-glycosylation of the identical peptide backbone found in the membrane form. Accordingly, samples of both rsCD26 and serum DPPIV were sequentially digested by neuraminidase (NANase II), by O-glycosidase, and then by PNGase F (removing NeuAc, O-linked and all N-linked oligosaccharides and poly-sialic acids). As shown in FIG. 2, the pattern of digestion is similar for rsCD26 and serum DPPIV, demonstrating that both have significant N-linked glycosylation but little if any O-glycosylation. Nevertheless, the deglycosylated backbone of serum DPPIV remains larger than that of rsCD26 (approximately 130 kDa in comparison with 90 kDa, the latter figure agreeing well with the 89 kDa predicted from the amino acid sequence), demonstrating that the higher molecular weight of the serum form is not due to hyperglycosylation. Staining for glycoprotein revealed that enzymatic deglycosylation resulted in removal of all carbohydrate residues detectable by periodic acid-Schiff's reagent (FIG. 2, lanes 9–12).

EXAMPLE III

Enzymatic Properties of Serum CD26

The DPPIV enzyme activities of the rsCD26 and serum DPPIV were analyzed by Michaelis-Menten kinetics by assessing kinetics of hydrolysis of substrate at different concentrations. Analysis using the Lineweaver-Burke transformation yielded an identical $K_m$ of 0.28 mM for Gly-Pro-pNA for both recombinant and serum DPPIV and the values for $V_{max}$ of 1.52 U/nmol rsCD26 and 0.65 U/nmol serum DPPIV were in the same range, using Gly-Pro-pNA as substrate. Inhibition by the specific DPPIV inhibitor Diprotin A was similar for both serum DPPIV and rsCD26, with an $IC_{50}$ of 0.125 mM for rsCD26, and 0.25 mM for serum DPPIV. To further exclude the possibility that we had purified irrelevant aminopeptidases which, working in concert or by sequential hydrolysis, could release the pNA chromophore from substrate, we tested a number of substrates which could be hydrolyzed by non-DPPIV aminopeptidases. One candidate for sequential hydrolysis is aminopeptidase M (3.4.11.2), but no hydrolysis of Ala-pNA, Arg-pNA or Leu-pNA was observed and activity by aminopolypeptidase (3.4.11.14) may be similarly excluded. The substrate succinyl-Gly-Pro-pNA was also not hydrolyzed. The only substrate apart from the dipeptide chromatogen Gly-Pro-pNA which could be hydrolyzed was Val-Ala-pNA, which was cleaved by both the serum DPPIV and rsCD26 (relative to rate of hydrolysis of Gly-Pro-pNA, hydrolysis of Val-Ala-pNA was 0.098 and 0.079, for rsCD26 and serum DPPIV, respectively). Although DPPIV primarily hydrolyses dipeptides with a proline in the penultimate position, it is well documented that alanine in the penultimate position may also render a dipeptide sequence susceptible to cleavage by DPPIV (8). The Gly-Pro-pNA substrate may also be a substrate for dipeptidylpeptidase II (DPPII), as may Val-Ala-pNA, but this enzyme has an acidic pH optimum (8). We determined the pH optima for both the rsCD26 and the serum DPPIV and showed them to be identical at pH8.5, while there was almost a complete inhibition of activity at acidic pH4.5–5, suggesting that we were not purifying a DPPII-like molecule.

EXAMPLE IV

Epitope Analysis

Figure 3:
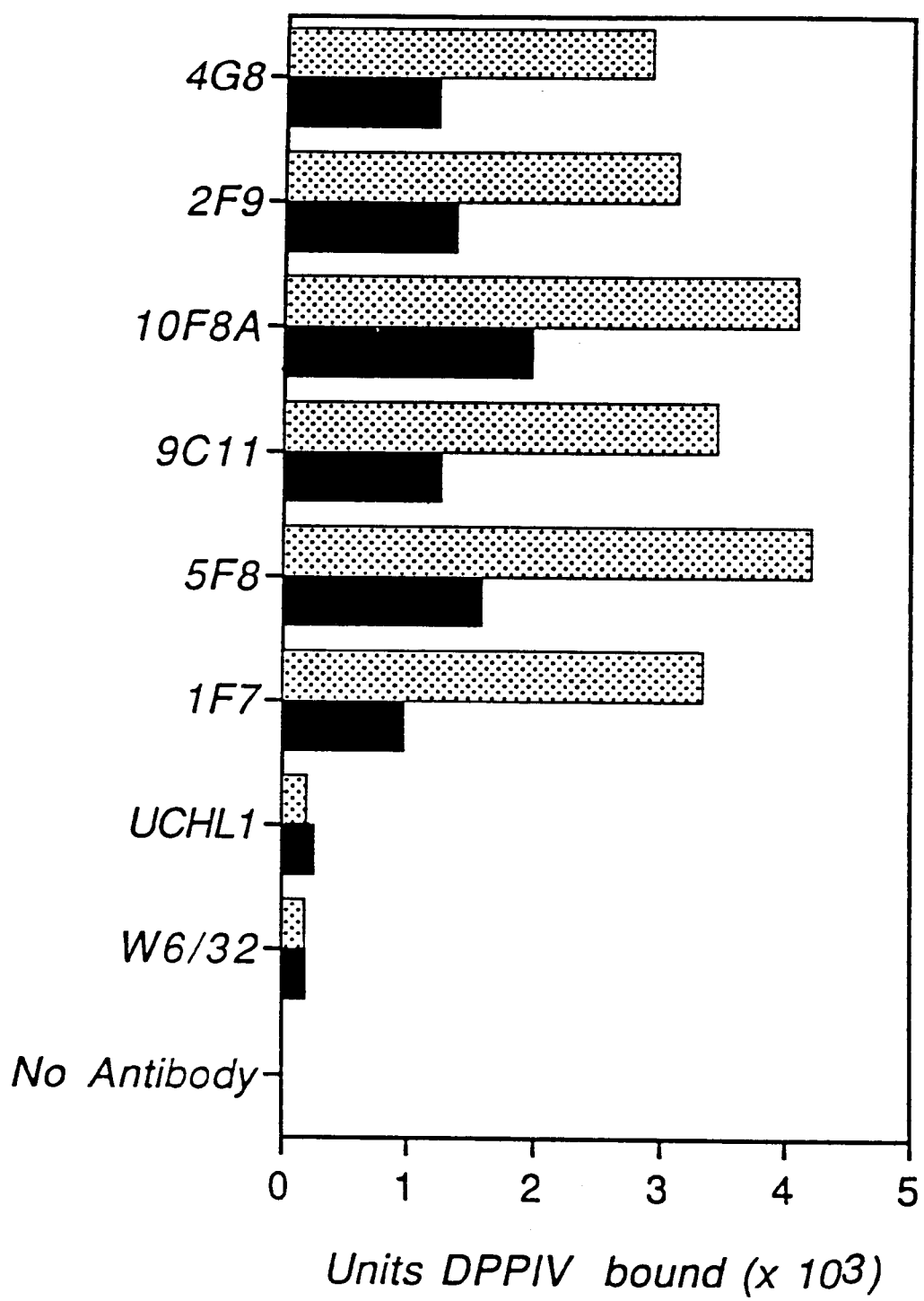
FIG. 3 shows the results of analysis of epitope expression by rsCD26 (light stipple) and serum DPPIV (heavy stipple). Units of enzyme activity represent the DPPIV activity of the CD26/DPPIV bound to CD26-specific antibodies immobilized on anti-mouse Ig-Sepharose beads. UCHL1 (anti-CD45RO) and W6/32 (anti-HLA Class I) are control antibodies.

In order to compare the antigenic sites of rsCD26 and serum DPPIV, we used a panel of monoclonal anti-CD26 antibodies developed in our laboratory which had been shown to detect 5 distinct antigenic epitopes of CD26 by cytofluorimetry and by cross-blocking using Surface Plasmon Resonance. Both serum DPPIV and rsCD26 were incubated with the murine monoclonal anti-CD26 antibodies (1F7, 5F8, 9C11, 2F9, and 4G8 which detect distinct epitopes, and 10F8A which detects an epitope shared by the 1F7 and 2F9 determinants) and with murine monoclonal control antibodies (W6/32 and UCHL1) after which the antibody-antigen complexes were removed from unbound material by binding to anti-mouse IgG Sepharose beads. Complexed CD26 was determined by DPPIV activity which was proportional to the amount of CD26/DPPIV immobilized (FIG. 3). The serum DPPIV and the rsCD26 both bind 1F7 10F8A, 5F8, 4G8 and 9C11. The complete panel of anti-CD26 antibodies can bind to both serum DPPIV and rsCD26, and despite the binding being greater to the recombinant form, the implication is that the two proteins share some structural motifs.

EXAMPLE V

N-terminal Sequencing of Tryptic Peptides of Serum DPPIV

N-terminal sequences of 10 peptides derived after tryptic digestion of reduced and alkylated serum DPPIV were determined. Of these, none revealed a complete identity with any sequence within available computerized databases. Nevertheless, 6 of the peptides revealed significant homology and similarity (using conservative substitutions) to a metalloendopeptidase (leishmanolysin), a serine endopeptidase (myeloblastin), a protein classified originally as a proteolytic plasminogen activator (neutral proteinase, of which the protease activity is now questionable), urokinase plasminogen activator, and chymotrypsin-like serine protease precursor.

EXAMPLE VI

Serum DPPIV is a Serine Proteinase

Figure 4:
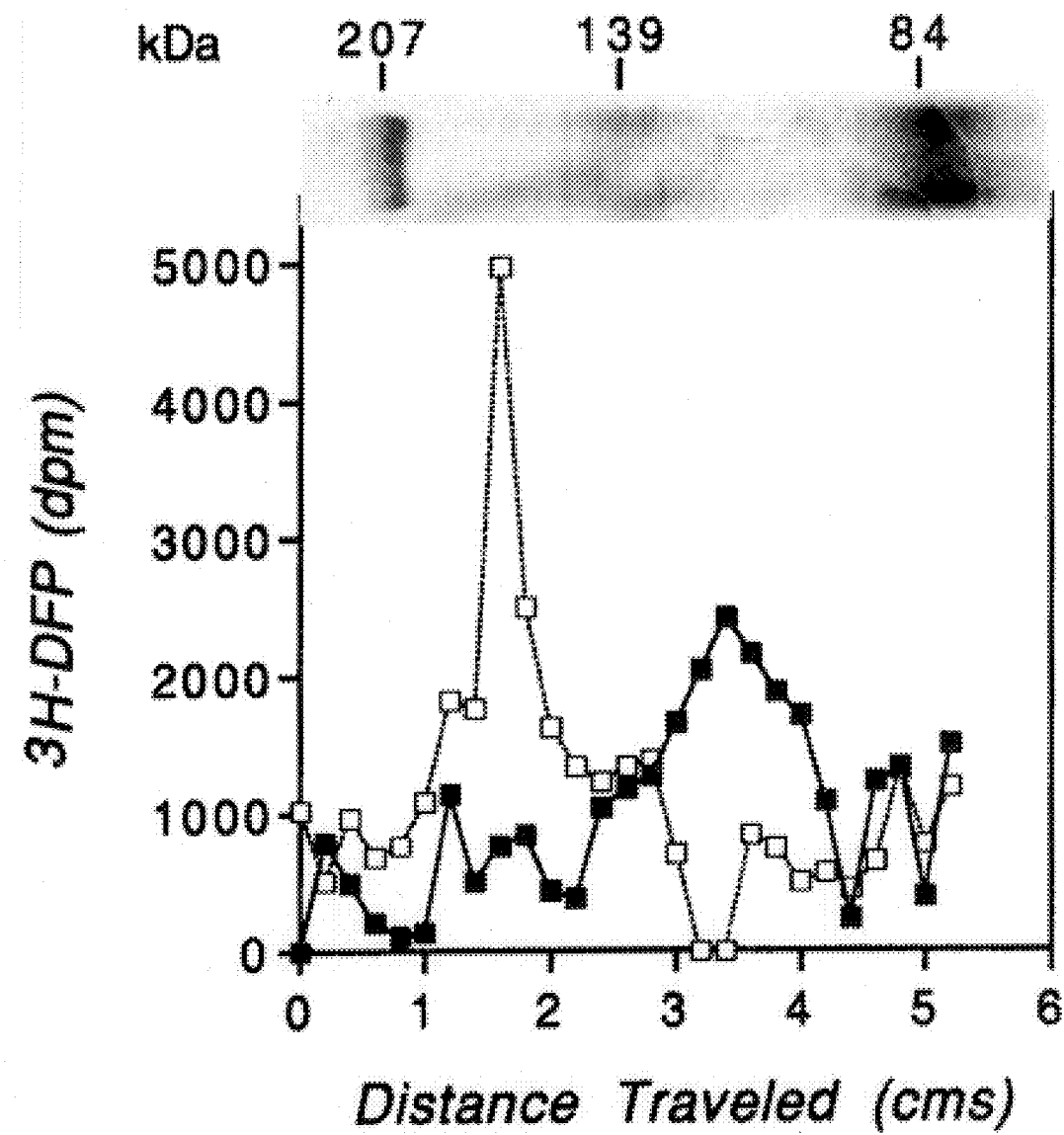
FIG. 4 shows $^3$H-diisopropylfluorophosphate ($^3$H-DFP) binding to rsCD26 (■) and serum DPPIV (□). Each lane was cut into 2 mm slices, each of which was dissolved in scintillation fluid and counted. The abcissa represents distance (cms) traveled in the gel and is correlated with the indicated molecular weight markers which were run on the same gel. The ordinate (dpm) represents the amount of $^3$H-DFP-labeled protein.

To determine the functional classification of serum DPPIV and compare it with rsCD26 which is known to be a serine proteinase, we incubated the serum DPPIV with $^3$H-DFP which binds to serines in the active site of serine proteinases. As shown in FIG. 4, the serum DPPIV could be labeled with DFP and formed a sharp peak around 175–180 kDa, while the rsCD26 was more broadly spread over the region of 105–115 kDa, which might be attributed to heterogenous glycosylation (18).

EXAMPLE VII

Figure 5A:
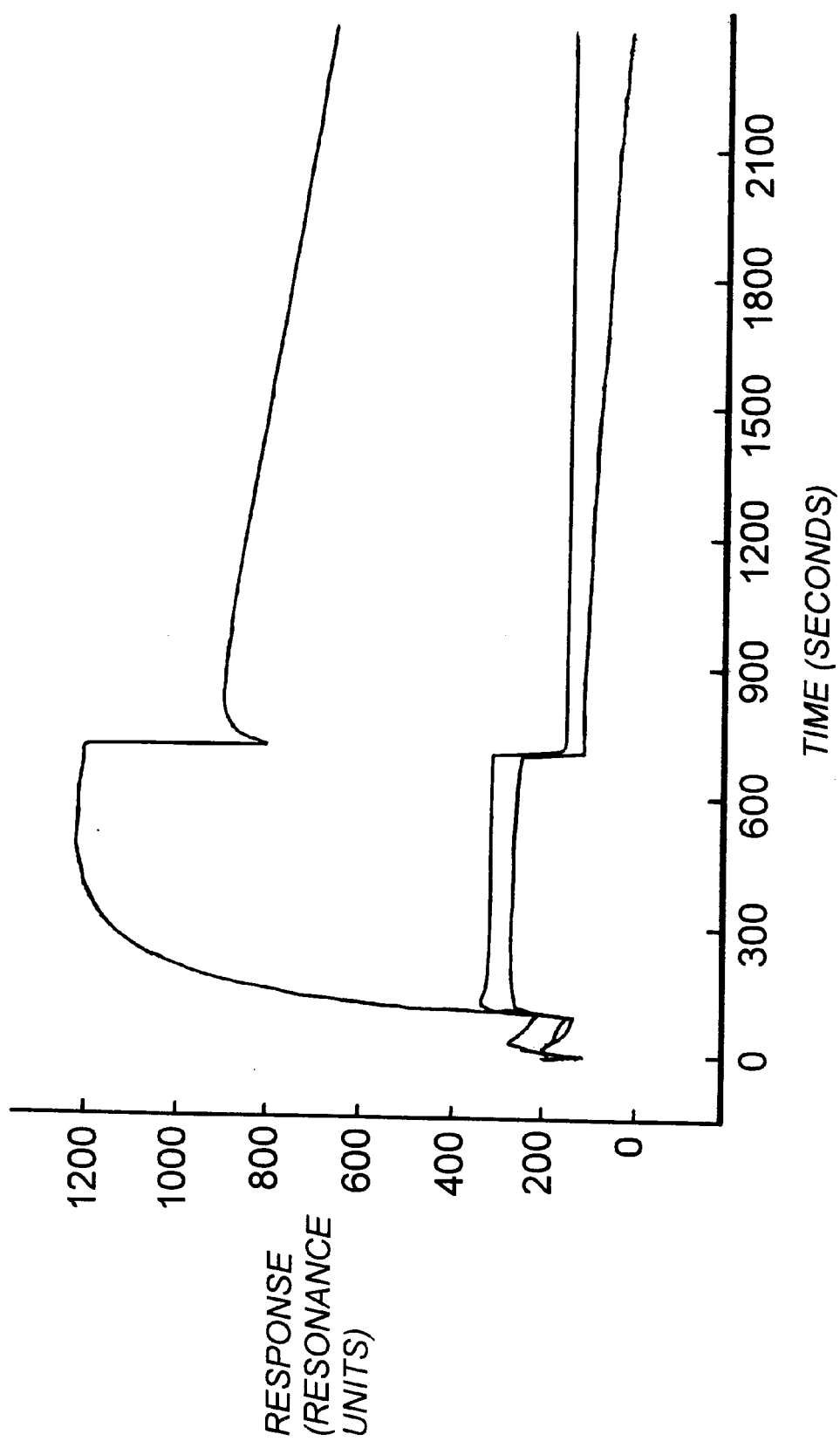
FIGS. 5A–5B show the results of analysis of adenosine deaminase binding of rsCD26 and serum DPPIV/CD26. Panel A: Analysis of ADA-binding of rsCD26 and serum DPPIV detected by Surface Plasmon Resonance. ADA (10 μg/ml in 10 mM HEPES, 100 mM NaCl, 0.050% Tween 20) was passed over a Control carboxymethyl dextran (CM) surface (lowest trace), over serum DPPIV (middle trace), and over rsCD26 (upper trace), both immobilised on a CM surface. One thousand Resonance Units (ordinate) represents approximately 1 ng/mm$^2$ of binding protein. Panel B: Analysis of ADA-binding of rsCD26 and serum DPPIV by immobilization with anti-ADA. rsCD26 and serum DPPIV, incubated with or without ADA, were allowed to interact with rabbit anti-ADA or Normal Rabbit Serum (Control), followed by removal of immune complexes with Protein A-Sepharose beads. DPPIV/CD26 complexed to the beads was determined by DPPIV enzyme activity. The light stippled bars represent untreated, and the heavy stippled bars represent deglycosylated, rsCD26 and serum DPPIV.
Figure 5B:
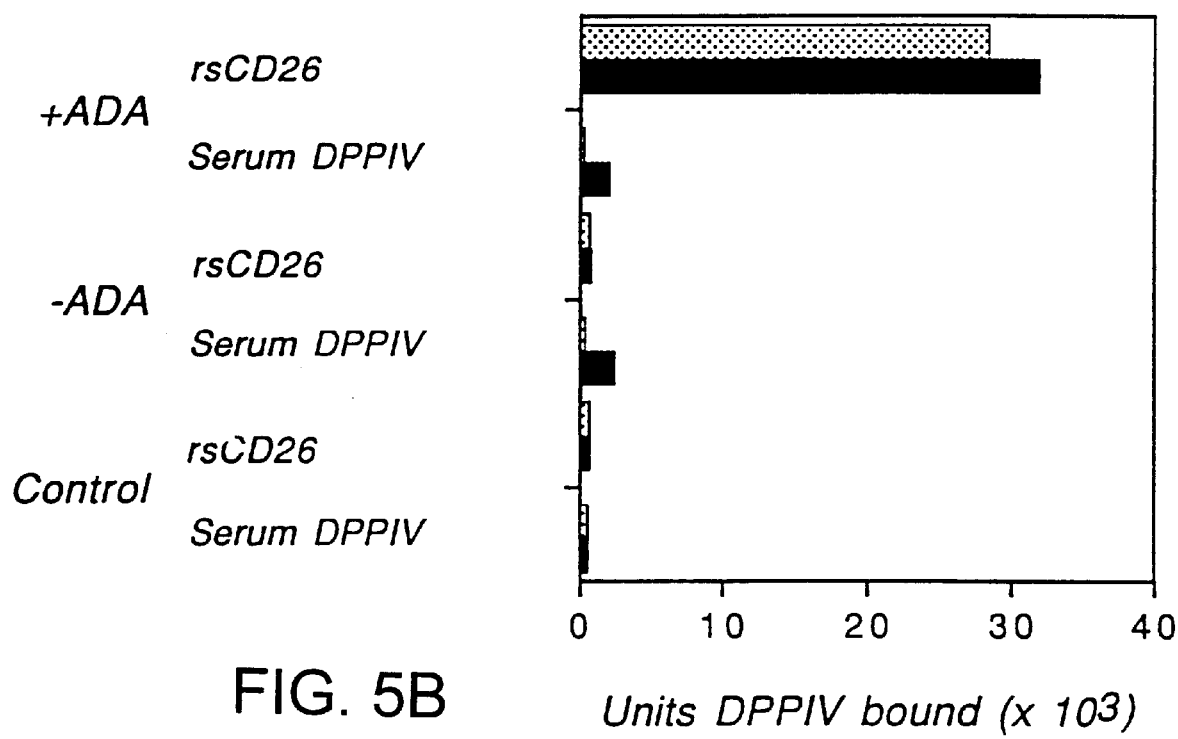

Binding of ADA-1 to CD26 rsCD26 has been shown previously to be identical to the membrane protein which binds ADA-1 (13, 22). We used two techniques to determine whether serum DPPIV binds ADA-1. The first technique utilized Surface Plasmon Resonance to measure the interaction of ADA-1 with serum or recombinant CD26 immobilized on a carboxymethyl dextran surface. It is clear that the rsCD26 has a high affinity for ADA-1 but that this is not so for serum DPPIV (FIG. 5A) which shows a binding profile similar to that of the Control. To confirm this, we utilized a technique whereby rabbit anti-ADA antibodies were incubated with rsCD26 or serum DPPIV, and the immune complexes formed were removed with Protein A Sepharose beads. Binding of ADA-1 to CD26 was then confirmed by detection of DPPIV activity associated with the extensively washed beads. In the absence of exogenously-added ADA-1 (FIG. 5B, "– ADA"), neither the rsCD26 nor the serum CD26 had any associated ADA-1 prior to the experiment. Upon addition of exogenous ADA (FIG. 5B, "+ ADA"), only the rsCD26 bound to the ADA, and no evidence of ADA-binding to serum DPPIV was observed. Although the rsCD26 DPPIV activity developed within 10 minutes of adding substrate, the samples were left for 24 hr after which time the samples incubated with serum CD26 had still not developed a signal above background, showing that the lack of ADA-binding was absolute, and not a relative difference. It is also of interest to note that deglycosylated rsCD26 is still able to bind ADA-1 as well as the untreated form, suggesting that the ADA binding site on rsCD26 is not in the heavily glycosylated region proximal to the membrane.

EXAMPLE VIII

T Cell Costimulatory Activity of CD26

Figure 6:
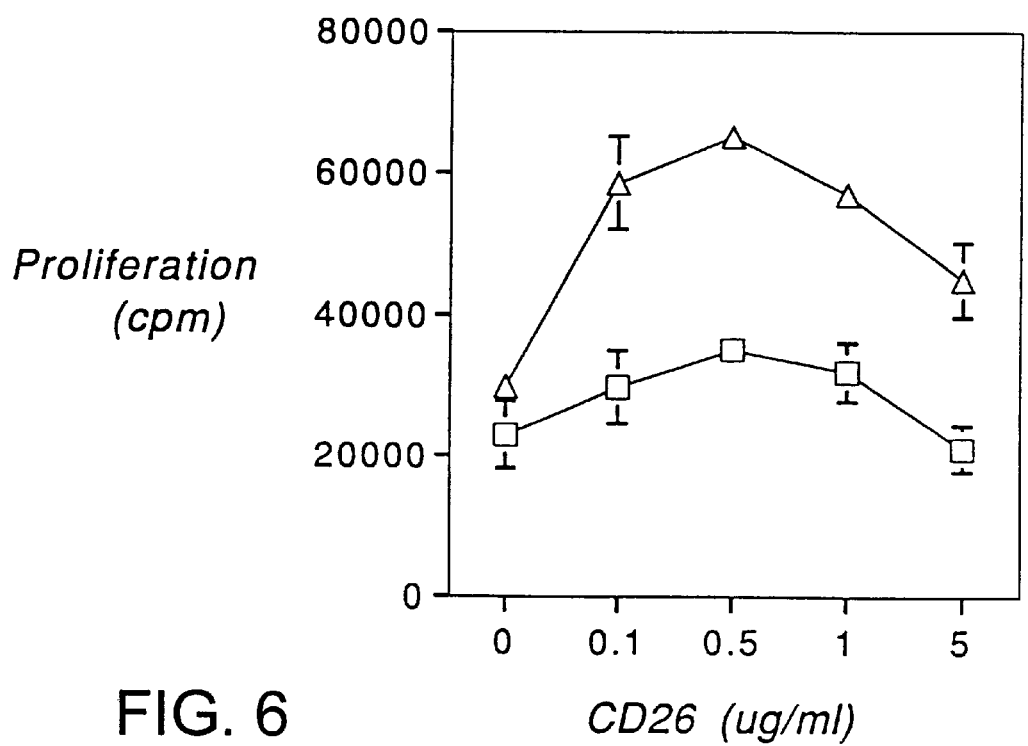
FIG. 6 shows T cell costimulatory activity developed by soluble DPPIV/CD26. rsCD26 (□) and serum DPPIV (Δ) were incubated with PBL and tetanus toxoid in medium supplemented with soluble CD26-depleted autologous plasma. Proliferation was assayed by measurement of cell-incorporated $^3$H-thymidine at 7 days. Vertical bars represent s.e.m. In the absence of tetanus toxoid, neither form of CD26/DPPIV had any effect upon the base response of 2351±108 c.p.m. (data not shown)

We have previously shown that rsCD26 is able to enhance the responses of peripheral blood leukocytes (PBL) to the recall antigen, tetanus toxoid (15). Accordingly, we tested whether serum DPPIV could also enhance the responses of PBL to tetanus toxoid. As shown in FIG. 6, the serum DPPIV was as capable as rsCD26 at costimulating the response to tetanus toxoid, with the peak response in the range 0.5 to 1 $\mu$g/ml. As we have routinely observed, concentrations of rsCD26 higher than 1 $\mu$g/ml tend to be inhibitory, and a similar phenomenon was observed for serum DPPIV. It is important to note here that all autologous plasma samples used as culture supplements during the incubation with recall antigen were precleared of endogenous CD26/DPPIV activity by pretreatment of the plasma samples with anti-CD26 antibody and removal of immune complexes with anti-mouse-IgG magnetic beads.

Materials and Methods
Recombinant Soluble CD26

The full extracellular domain of T cell membrane-expressed CD26 (rsCD26) was obtained as a soluble secreted product from transfected CHO cells as described previously (15). The transfected CHO cells were grown in serum-free CHO-SFM medium to confluence (Life Technologies Inc., Gaithersburg, Md.). Sodium azide (0.1% w/v final) was added to the rsCD26-containing conditioned medium which was passed at 1 ml/min over a 38×1.5 cm concanavalin A (ConA)—agarose column (Sigma, St Louis, Mo.) equilibrated in 2× phosphate-buffered saline (2×PBS; 30.8 mM NaCl, 0.54 mM $Na_2HPO_4.7H_2O$, 0.31 mM $KH_2PO_4$; pH6.8) at room temperature (as were all subsequent column procedures). After washing with 5 column volumes of 2×PBS, bound glycoprotein was eluted with 2×PBS containing 200 mM α-methylmannoside (Sigma) and dialyzed extensively against 50 mM sodium acetate buffer, pH4.65. After equilibrating a 8.5×2.5 cm s-Sepharose (Pharmacia, Piscataway, N.J.) ion exchange column in 50 mM sodium acetate, pH4.65 (equilibration buffer), the DPPIV-active ConA eluate was then loaded at 1 ml/min. The column was then washed with 10 column volumes of equilibration buffer and eluted with a 0–1M NaCl gradient in equilibration buffer. The rsCD26 elutes as a clean peak at 50 mM NaCl and all eluted DPPIV activity was associated with this peak.

DPPIV Activity

The primary substrate used for determining DPPIV activity in all assays was Gly-Pro-p-nitroanilide (Gly-Pro-pNA; Sigma), which is hydrolyzed by DPPIV to release pNA absorbing strongly at 405 nm. Kinetic assays were performed using varying amounts of substrate in order to obtain estimates of the $K_m$ and $V_{max}$ using standard Michaelis-Menten kinetics. For screening assays of DPPIV activity, 150 ml of substrate was used at 1 mg/ml (2 mM final concentration) in phosphate buffer (pH7.6, 100 mM) in 96 well flat-bottomed microtiter plates together with 10 ml of appropriately diluted sample. For samples obtained after elution from the s-Sepharose column, the pH was raised to pH7.6 by addition of 25 $\mu$l of 1M Tris-HCl, pH7.6 to the reaction mixture. One unit (U) of enzyme activity was defined as the amount of enzyme that cleaved 1 mmol of Gly-Pro-pNA/min at pH7.6 and 20° C. Inhibition of the hydrolysis of Gly-Pro-pNA was determined in the presence of the specific DPPIV inhibitor Diprotin A (Bachem, King of Prussia, Pa.). To test for the presence of non-DPPIV peptide hydrolase activity, the following substrates were used (all obtained from Bachem): Leu-pNA, Ala-pNA, Arg-pNA, succinyl-Gly-Pro-pNA, Gly-Arg-pNA, and Val-Ala-pNA (a weak DPPIV substrate). The pH optimum was determined substituting phosphate buffer (100 mM, pH4.5–pH9) in place of standard incubation buffer.

Serum DPPIV

Serum DPPIV was prepared by isolating from 100 ml of pooled normal human male AB serum the fraction of protein precipitated by 50–70% saturated ammonium sulfate. After extensive dialysis against 50 mM acetate buffer, pH4.65, the material was passed onto, and eluted from, a s-Sepharose column in an identical manner to that described above for rsCD26. The DPPIV-positive fractions were pooled and dialyzed against 2×PBS prior to binding and elution from a ConA-agarose column as described above for rsCD26. The ConA eluate was dialyzed against acetate equilibration buffer and re-applied to the s-Sepharose column which was then washed with 10 volumes of equilibration buffer. The DPPIV activity was eluted by a 0–0.5M NaCl gradient in equilibration buffer and all DPPIV activity was found in the 10 mM–50 mM NaCl eluate (determined by conductance). The eluted material was then concentrated to 1–2 ml using 10 kDa cut-off centrifugal concentrators (Centriprep 10; Amicon, Beverley, Mass.) and was then applied to a preparative native 7.5% acrylamide gel buffered with Tris-Glycine. After electrophoresis, the gel was cut horizontally into 1 mm strips and the >30 kDa material was extracted from the gel slices by electroelution (Model 422; BioRad, Melville, N.Y.). The eluted material expressing DPPIV activity was characterized by running on a 7.5% SDS-PAGE gel under reducing conditions followed by silver staining (Amersham, Arlington Heights, Ill.). The molecular weight of serum DPPIV was also determined by its application (50 µg in 100 ml PBS) on to a 100×1.5 cm Superdex 200 column (Pharmacia) equilibrated in PBS after calibration using Blue Dextran (for void volume), thyroglobulin (669 kDa), apoferritin (443 kDa), alcohol dehydrogenase (150 kDa) and bovine serum albumin (66 kDa), all obtained from Sigma. Flow rate was 0.4 ml/min, protein elution was monitored by optical density at 280 nm, and the DPPIV-containing fractions were localized by ability to hydrolyze Gly-Pro-pNA using the standard conditions described above.

Enzymatic Deglycosylation

Sequential deglycosylations were performed using recombinant N-acetylneuraminidase II (NANase II; 10 mU/10 µg substrate protein), O-glycosidase (2 mU/10 µg substrate protein), and Peptide:N-glycosidase F (PNGase F; 5 mU/10 µg substrate protein) using buffers and reagents supplied (Glyko, Novato, Calif.). Briefly, the NANase II (removing a[2-3]-, a[2-6]-, and a[2-8]-linked NeuAc) and O-glycosidase digestions were performed for 1 hr at 37° C. in 50 mM sodium phosphate, pH6.0. The pH of the samples was then raised by addition of $Na_2HPO_4$ to 0.125M final, pH8.0, followed by boiling in the presence of SDS and β-mercaptoethanol for 5 min to denature the protein. Nonidet P-40 (NP-40, 2.5 µl/40 µl sample) was added prior to incubation with PNGase F for 3 hr at 37° C. which removed N-linked tri- and tetra-antennary complex-type oligosaccharide chains, poly-sialic acids, and high-mannose and hybrid-oligosaccharide chains. The samples were again incubated with SDS-PAGE reducing sample buffer at 100° C. prior to electrophoresis on 10% acrylamide gels. To check for complete deglycosylation, the enzyme-treated proteins were stained for carbohydrate moieties in 10% SDS-PAGE gels by oxidation with periodic acid followed by staining with Schiff's reagent (Sigma).

Epitope Analysis

1 µg of serum DPPIV or rsCD26 was incubated in 100 µl of PBS containing 0.05% Tween 20 (Sigma; PBS-Tween) together with 5 µg purified Control or anti-CD26 antibodies for 1 hour at 4° C. with rotation. Control murine monoclonal antibodies used were W6/32 (anti-β2-microglobulin/HLA Class I, $IgG_2$, ref. 16) and UCHL1 (anti-CD45RO, $IgG_{2a}$, ref. 17). The anti-CD26 murine monoclonal IgG antibodies used were 1F7 ($IgG_1$) and 5F8 ($IgG_1$) described previously (2, 18) and 10F8A, 9C11, 4G8, and 2F9 (all $IgG_1$) which were produced in our laboratory after immunization of mice with CD26-transfected 300.19 cells, a murine pre-B cell lymphoma line. All antibodies were purified by binding to and elution from Protein A-Sepharose (Pharmacia). By epitope analysis using Surface Plasmon Resonance (BIACore, Pharmacia Biosensor AB), 5F8, 2F9, 4G8, 9C11 and 1F7 detected 5 unique epitopes while 10F8A was blocked by 1F7 and 2F9. Anti-mouse IgG-agarose beads (Sigma; 50 µl) were added to each sample and incubated for a further 16 hr at 4° C. with rotation followed by 5 washes of the beads with PBS-Tween to remove unbound CD26 and antibody. Twenty µl of the washed beads were then incubated in duplicate together with Gly-Pro-pNA (2 mM final concentration). The enzyme activity, determined as hydrolysis and release of pNA measured at 405 nm, of the antibody-immobilized CD26/DPPIV provided a relative measure of the affinity of the particular antibody for CD26.

Peptide and Sequence Analysis

For N-terminal sequencing, 50 µg (~280 pmol) of serum DPPIV was electrophoresed on a 7.5% SDS-PAGE gel, electrotransfered to a PVDF membrane (0.45 mm; BioRad), and stained with 0.1% Ponceau S in 5% acetic acid (Sigma). After cutting out the stained band at 175–180 kDa, protein was eluted from a small piece of membrane for amino acid analysis to estimate the amount of transferred protein. The protein was then subjected to tryptic digestion on the PVDF membrane and the products were resolved by narrow-bore reverse phase HPLC as described (19). Peaks suitable for N-terminal sequencing were selected, checked for molecular weight by matrix-assisted laser desorption mass spectroscopy and sequence determined using a Model 477A Protein Sequencer linked to a Model 120A PTH-amino acid analyzer (Applied Biosystems, Foster City, Calif.). All sequence analysis was performed using the GCG Unix package (Genetics Computer Group, Madison, Wis.).

Affinity-labeling of Enzyme Active Site

To determine whether serum DPPIV is a serine protease similar to rsCD26, the active sites of both proteins (5 µg in 20ml 100 mM Tris-HCl, pH8.0) were labeled with 25 µCi $^3$H-di-isofluorophosphate (DFP, 1 mCi/ml; New England Nuclear, Boston, Mass.) for 24 hr at 37° C. after which the proteins were separated by SDS-PAGE (7.5%). The gel was fixed in 25% isopropanol/10% acetic acid and 2×10 mm slices of the lanes containing radiolabeled sample were cut out, homogenized in 1.5 ml polypropylene tubes and the slurries were incubated with 1 ml of scintillation cocktail (Atomlight; New England Nuclear) for 5 days with occasional shaking until all material had entered into solution. Further scintillation fluid (2 ml) was added and the samples were counted in a b-scintillation counter.

CD26 Binding to Adenosine Deaminase (ADA-1)

Purified serum DPPIV or rsCD26 (50 µg/ml in 20 mM acetate buffer, pH 4.5) was immobilized on the carboxylmethyl dextran surface of a CM5 Sensor chip by N-hydroxysuccinimide/carbodiimide-mediated amine coupling (BIACore, Pharmacia Biosensor AB). The ability of bovine adenosine deaminase (ADA-1, 10 µg/ml in 10 mM HEPES pH7.4, 100 mM NaCl, 0.05% Tween 20) to bind to the CD26-coated surface was determined by measuring Surface Plasmon Resonance (20). In a separate technique, and to simultaneously determine whether adenosine deaminase was already bound to serum DPPIV, samples of serum DPPIV and rsCD26 (1 µg/ml) were incubated for 30 min at 4° C. in the presence or absence of ADA-1 (10 µg/ml in Tris Buffered Saline, pH7.4, containing 0.1% Tween; TTBS), followed by an incubation with a polyclonal rabbit anti-human ADA (Dr J. Kameoka, Dana Farber Cancer Institute; diluted 1:20 in TTBS) or normal rabbit serum control. Protein A-Sepharose (Sigma; 50 µl) was added and the samples incubated overnight while rotating at 4° C. After 4 washes in TTBS, the Protein A-Sepharose beads were tested for DPPIV activity by incubation with Gly-Pro-pNA (2 mM final concentration).

Proliferation Assays

Peripheral blood leukocytes were isolated from donors tested previously for positive proliferative responses to tetanus toxoid, where such responses could be further enhanced by addition of rsCD26. PBL were resuspended at $5×10^4$ in 200 µl RPMI 1640 containing 10 % autologous serum depleted of endogenous CD26 by batch incubation with anti-CD26 antibodies as described previously (15), with or without tetanus toxoid (Connaught Laboratories, Swiftwater, Pa.; 10 µg/ml) and serum DPPIV or rsCD26 at the indicated concentrations and incubated in round-bottomed 96 well microtiter plates for 7 days at 37° C. in a humidified 7.5% $CO_2$ atmosphere. Each well was pulsed with 1 µCi tritiated thymidine (New England Nuclear) and was incubated for a further 24 hr before harvesting and counting incorporated thymidine using a β-scintillation counter.

Use

Soluble serum DPPIV/CD26 and variants thereof are generally useful as immune response-stimulating therapeutics as described in U.S. patent application Ser. No. 08/388,221, the whole of which is incorporated by reference herein. For example, the compounds of the invention can be used for treatment of disease conditions characterized by immunosuppression: e.g., AIDS or AIDS-related complex, other virally- or environmentally-induced conditions, and certain congenital immune deficiencies. The compounds may also be employed to increase immune function that has been impaired by the use of immunosuppressive drugs such as certain chemotherapeutic agents, and therefore are particularly useful when given in conjunction with such drugs. When given as an adjuvant in conjunction with a vaccine antigen, the compounds of the invention will boost the immune response triggered by the vaccine and thus increase the vaccine's protective potency. This would be particularly beneficial where the vaccinee is incapable of generating an optimal immune response without the use of such an adjuvant, as is the case for newborns or for persons undergoing renal dialysis or transplantation, or where the vaccine antigen is one which is poorly immunogenic.

Generally, the compounds of the invention will be suspended in a pharmaceutically-acceptable carrier (e.g., physiological saline) and administered orally or by intravenous infusion, or injected subcutaneously, intramuscularly, or intraperitoneally. Optimal formulation and dosage can be readily determined by one of ordinary skill in the art of pharmacology, taking into account such factors as the biological half-life of the compound and the degree of immunostimulation desired. It is expected that a typical dose for a severely immunocompromised patient will be approximately 0.01 to 100 μg/kg/day. When utilized as a vaccine adjuvant, a typical single dose of the compound of the invention would be 0.1 to 100 μg.

Alternatively, peripheral blood lymphocytes can be withdrawn from the patient and treated with the serum DPPIV/CD26 compound of the invention (whether in soluble form or attached to a solid support by standard methodologies) ex vivo, prior to introducing the newly-stimulated lymphocytes into the same or a different patient.

TABLE 1

Purification of CD26/DPPIV from normal human serum[1]

|  | Protein (mg) | Total Activity[2] (units) | Specific Activity (units/mg) | Yield (%) | Fold Purification |
|---|---|---|---|---|---|
| Original serum | 8900 | 3.091 | $3.47 \times 10^{-4}$ | 100 | 1 |
| 50–70% Ammonium Sulfate Cut | 2648 | 2.258 | $8.53 \times 10^{-4}$ | 73.1 | 2.46 |
| s-Sepharose | 303 | 1.745 | $5.76 \times 10^{-3}$ | 56.5 | 16.58 |
| concanavalin A | 12.49 | 1.434 | 0.115 | 46.4 | 330.6 |
| s-Sepharose | 3.01 | 1.242 | 0.413 | 40.2 | 1188 |
| Preparative Native Electrophoresis | 0.175 | 0.312 | 1.78 | 10.1 | 5125 |

[1]100 ml of normal human male AB serum
[2]One unit is defined as the amount of enzyme cleaving 1 mmol of Gly—Pro—pNA/min under the assay conditions used

TABLE 2

N-terminal sequences determined for serum DPPIV after proteolytic digestion. Dashes (--) indicate N-terminal or C-terminal extensions, a single dash (-) indicates that a gap has been inserted for alignment. A 'x' indicates that an amino acid could not be reliably identified at that position. Similarity was determined by conservative replacement using the 'FASTA' program (Genetics Computer Group, Madison, WI).

|  |  |  | % Identity/ Similarity |
|---|---|---|---|
| 1. | serum DPPIV | LTGSSGFTD GPGNYK (SEQ ID NO: 1) | 44/75 |
|  | 3.4.24.36[a] | --VRGSSGYVAC TPGQRV-- (SEQ ID NO: 7) |  |
| 2. | serum DPPIV | YDVDTQMxTI LK (SEQ ID NO: 2) | 33/92 |
|  | 3.4.21.76[b] | --YDAENKLNKI LL-- (SEQ ID NO: 8) |  |
| 3. | serum DPPIV | GFNLIIT (SEQ ID NO: 3) | 71/71 |
|  | Protease III[c] | --GFNLITK-- (SEQ ID NO: 9) |  |
| 4. | serum DPPIV | QNALLARLT (SEQ ID NO: 4) | 67/67 |
|  | 3.4.21.73[d] | MRALLARLL-- (SEQ ID NO: 10) |  |
| 5. | serum DPPIV | GDQHTDCYSC TAN-TNDCHW C (SEQ ID NO: 5) | 30/57 |
|  | 3.4.21.73 | --PQNERQCYSC KGNSTHCGSS E-- (SEQ ID NO: 11) |  |
| 6. | serum DPPIV | SGQISIFG (SEQ ID NO: 6) | 63/68 |
|  | 3.4.21.-[e] | --SGHICIFE-- (SEQ ID NO: 12) |  |

[a]EC 3.4.24.36: leishmanolysin precursor (cell surface protease)
[b]EC 3.4.21.76: myeloblastin (proteinase 3 precursor, Wegener's autoantigen)
[c]Protease III: originally classified as EC 3.4.24.4 (neutral proteinase).
[d]EC 3.4.21.73: urokinase plasminogen activator
[e]EC 3.4.21.-: chymotrypsin-like serine proteinase precursor

| Abbreviations: |  |
|---|---|
| ADA-1 | adenosine deaminase type I |
| ADA-CP | adenosine deaminase complexing protein |
| ConA | concanavalin A |
| DFP | di-isopropylfluorophosphate |
| DPPII | dipeptidylpeptidase II |
| DPPIV | dipeptidylpeptidase IV |
| NANase II | recombinant neuraminidase II |
| NP-40 | Nonidet P-40 |
| PBL | peripheral blood leukocytes |
| PBS | phosphate-buffered saline |
| pNA | p-nitroanilide |
| PNGase F | recombinant Peptide:N-glycosidase F |
| PVDF | polyvinylidene difluoride |
| rsCD26 | recombinant soluble CD26 |
| SDS-PAGE | SDS polyacrylamide gel electrophoresis |

REFERENCES

1. Fox et al., J. Immunol. 133:1250–1256 (1984).
2. Morimoto et al., J. Immunol. 143:3430–3439 (1989).
3. Hafler et al., J. Immunol 137:414–418 (1986).
4. Stein et al., "Leukocyte Typing IV" (Knapp, W., Oxford University Press, Oxford, Great Britain (1989).
5. Hegen et al., J. Immunol 144:2908–2914 (1990).
6. Ulmer et al., Scand. J. Immunol. 31:429–435 (1990).
7. Tanaka et al., Proc. Natl. Acad. Sci. USA 90:4586–4590 (1993).
8. Yaron et al., Crit. Rev. Biochem. Mol. Biol. 28:31–81 (1993).
9. Heymann et al., FEBS Lett. 91:360–364 (1978).
10. Dang et al., J. Immunol. 144:4092–4100 (1990).
11. Tanaka et al., J. Immunol. 149:481–486 (1992).
12. Torimoto et al., J. Immunol. 147:2514–2517 (1991).
13. Kameoka et al., Science 261:466–469 (1993).
14. Buc et al., Eur. J. Immunol. 20:611–615 (1990).

15. Tanaka et al., Proc. Natl. Acad. Sci (USA) 91:3082–3086 (1994).
16. Barnstable et al., Cell 14:9–20 (1978).
17. Terry et al., Immunology 64:331–336 (1988).
18. Torimoto et al., Mol. Immunol. 29:183–192 (1992).
19. Lane et al., J. Prot. Chem. 10:151–160 (1991).
20. Malmqvist et al., Nature 361:186–187 (1993).
21. Nakanishi et al., Biological Mass Spectrometry 23:230–233 (1994).
22. Morrison et al., J. Exp. Med. 177:1135–1143 (1993).
23. Kyouden et al., J. Biochem. 111:770–777 (1992).
24. Hino et al., Clin. Chem. 22:1256–1261 (1976).
25. Vanhoof et al., Eur. J. Clin. Chem. Clin. Biochem. 30:333–338 (1992).
26. Stancikova et al., Clin. Exp. Rheumatol. 10:381–385 (1992).
27. Hama et al., Clin. Chim. Acta. 113:217–221 (1981).
28. Chikuma et al., Biol. Chem. Hoppe-Seyler 371:325–330 (1990).
29. Fleischer et al., Immunology Today 15:180–184 (1994).
30. Schrader et al., J. Biol. Chem. 254:11964–11968 (1979).
31. Darmoul et al., Ann. Hum. Genet. 54:191–197 (1990).
32. Chobert et al., J. Biol. Chem. 265:2352–2357 (1990).
33. Wada et al., Proc. Natl. Acad. Sci. (USA) 89:197–201 (1992).
34. Scanlan et al., Proc. Natl. Acad. Sci. (USA) 91:5657–5661 (1994).
35. Bernard et al., Biochemistry 33:15204–15214 (1994).
36. Ollis et al., Protein Engineering 5:197–211 (1992).
37. Hirschhorn et al., "Isozymes: Current Topics in Biological and Medical Research" 4 (1980).
38. Niedzwicki et al., Am. J. Hematol. 37:152–155 (1991).
39. Ungerer et al., Clin. Chem. 38:1322–1326 (1992).
40. Matsuda et al., Clin. Infect. Dis. 16:260–264 (1993.

OTHER EMBODIMENTS

The invention also includes fragments and analogs of serum DPPIV/CD26. The term "analogs" refers to polypeptide fragments of serum DPPIV/CD26 having conservative and/or non-conservative substitutions for some of the amino acids of naturally-occurring serum DPPIV/CD26, having D-amino acids in place of some or all of the corresponding L-amino acids, or having non-peptide bonds in place of some of the peptide bonds of the naturally occuring form. Techniques for producing such analogs are well known in the art, and can be readily accomplished by those of ordinary skill. Preferably at least 85%, more preferably at least 95%, and most perferably at least 99%, of the amino acids in the analog are identical to the corresponding ones in the naturally occuring form. It is important that the substitutions do not eliminate the ability of the polypeptide fragment to interfere with the naturally occurring association between CD26 and CD45, or the ability of the compound to stimulate proliferation of lymphocytes. In some instances, the removal of peptide bonds from a polypeptide compound is a desirable goal because the presence of such bonds may leave the compound susceptible to attack by proteolytic enzymes. Additionally, such peptide bonds may affect the biological availability of the resulting therapeutic molecules. The removal of peptide bonds is part of a process referred to as "depeptidization". Depeptidization entails such modifications as replacement of the peptide bond (—CONH—) between two given amino acids with a spatially similar group such as —CH$_2$CH$_2$—, CH$_2$—O—, —CH=CH—OR —CH$_2$S—, generally by incorporating a non-peptide mimetic of the dipeptide into the chemically synthesized analog of the invention.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A substantially pure human glycoprotein having a molecular weight of approximately 175 kDa, as determined either by sodium dodecyl sulfate polyacrylamide gel electrophoresis (SDS-PAGE) or by matrix-assisted laser desorption mass spectrometry, the polypeptide portion of the glycoprotein having a molecular weight of approximately 130 kDa, wherein said glycoprotein exhibits functional dipeptidylpeptidase IV (DPPIV) activity but not Adenosine Deaminase Type-1 (ADA-1) binding activity.

2. A substantially pure protein having a molecular weight of approximately 130 kDa, said protein being the polypeptide portion of the glycoprotein of claim 1.

3. The glycoprotein of claim 1, said glycoprotein being part of a 570 kDa complex.

4. The glycoprotein of claim 1, said glycoprotein having N-linked glycosylation but not O-linked glycosylation.

5. The glycoprotein of claim 1, wherein said glycoprotein has the structure of a glycoprotein obtained from normal human serum.

6. A therapeutic composition comprising the glycoprotein of claim 1 in a pharmaceutically acceptable carrier substance.

7. A method for enhancing the immune response of an individual comprising administering to said individual an amount of the therapeutic composition of claim 6 sufficient to enhance the individual's immune response.

8. A polypeptide fragment of the glycoprotein of claim 1, said polypeptide fragment exhibiting functional DPPIV activity but not ADA-1 binding activity said polypeptide fragment further being capable of stimulating proliferation of lymphocytes.

9. The glycoprotein of claim 1, wherein the glycoplotein costimulates a T cell response.

10. The glycoprotein of claim 1, wherein the glycoprotein has the structure of a protein secreted by activated T cells.

11. The method of claim 7, further comprising administering a bacterial antigen to the individual.

12. The method of claim 11, wherein the bacterial antigen is selected from the group consisting of tetanus toxoid, diphtheria toxoid, pertussin toxoid, and live but attenuated bacteria.

13. The method of claim 7, further comprising administering a viral antigen to the individual.

* * * * *

UNITED STATES PATENT AND TRADEMARK OFFICE
CERTIFICATE OF CORRECTION

PATENT NO. : 6,325,989 B1
DATED : December 4, 2001
INVENTOR(S) : Chikao Morimoto, Jonathan S. Duke-Cohan and Stuart F. Schlossman It is certified that error appears in the above-identified patent and that said Letters Patent is hereby corrected as shown below:

<u>Title page, Item [54] and Column 1, line 2,</u>
In the title, add -- NOVEL -- as first word and delete "(CD26)"

<u>Column 3,</u>
Line 30, insert -- sodium dodecyl sulfate polyacrylamide gel electrophoresis -- after "by" and delete same on lines 32 and 33

<u>Column 4,</u>
Line 3, replace "0.050%" with -- 0.05% --

<u>Column 16,</u>
Line 17, replace "YDAENKLNKI" with -- YDAENKLN<u>D</u>I --
Line 29, replace "$^4$EC" with -- $^d$EC --

<u>Column 22,</u>
Line 41, insert -- , -- after "activity"
Line 44, replace "glycoplotein" with -- glycoprotein --

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,325,989 B1
DATED         : December 4, 2001
INVENTOR(S)   : Chikao Morimoto, Jonathan S. Duke-Cohan and Stuart F. Schlossman It is certified that error appears in the above-identified patent and that said Letters Patent is hereby corrected as shown below:

<u>Title page, Item [54] and Column 1, line 2,</u>
In the title the word "(CD26)" (as deleted by Certificate of Correction issued August 26, 2003) should be reinstated.

Title page,
Item [56], References Cited, OTHER PUBLICATIONS, page 2, after "Deaminase" remove ",".

<u>Column 3,</u>
Line 30, insert -- sodium dodecyl sulfate polyacrylamide gel electrophoresis -- after "by" and delete same on lines 32 and 33

<u>Column 4,</u>
Line 3, replace "0.050%" with -- 0.05% --

<u>Column 16,</u>
Line 17, replace "YDAENKLNKI" with -- YDAENKLN<u>D</u>I --
Line 29, replace "$^4$EC" with -- $^d$EC --

<u>Column 22,</u>
Line 41, insert -- , -- after "activity"
Line 44, replace "glycoplotein" with -- glycoprotein --

This certificate supersedes Certificate of Correction issued August 26, 2003

Signed and Sealed this

Ninth Day of September, 2003

JAMES E. ROGAN
*Director of the United States Patent and Trademark Office*